United States Patent
Czerwinska et al.

(10) Patent No.: US 9,682,056 B2
(45) Date of Patent: Jun. 20, 2017

(54) OLEACEIN FOR TREATING OR PREVENTING DISEASES RESULTING FROM ATHEROSCLEROTIC PLAQUES

(71) Applicant: Warszawski Uniwersytet Medyczny, Warsaw (PL)

(72) Inventors: Monika Ewa Czerwinska, Legionowo (PL); Anna Karolina Kiss, Warsaw (PL); Marek Aleksy Naruszewicz, Zalesie Gorne (PL); Agnieszka Filipek, Podkowa Lesna (PL)

(73) Assignee: Warszawski Uniwersytet Medyczny, Warsaw (PL)

( * ) Notice: Subject to any disclaimer, the term of this patent is extended or adjusted under 35 U.S.C. 154(b) by 143 days.

(21) Appl. No.: 14/356,172

(22) PCT Filed: Jul. 13, 2013

(86) PCT No.: PCT/EP2013/064869
§ 371 (c)(1),
(2) Date: Jul. 27, 2015

(87) PCT Pub. No.: WO2014/012871
PCT Pub. Date: Jan. 23, 2014

(65) Prior Publication Data
US 2016/0008311 A1    Jan. 14, 2016

(30) Foreign Application Priority Data
Jul. 14, 2012   (PL) .......................................... 399962

(51) Int. Cl.
*A61K 36/00*    (2006.01)
*A61K 31/19*    (2006.01)
*A61K 31/222*   (2006.01)
*A61K 36/638*   (2006.01)

(52) U.S. Cl.
CPC ............ *A61K 31/222* (2013.01); *A61K 31/19* (2013.01); *A61K 36/638* (2013.01)

(58) Field of Classification Search
CPC .............................. A61K 31/19; A61K 36/638
USPC .......................................... 514/557; 424/774
See application file for complete search history.

(56) References Cited

FOREIGN PATENT DOCUMENTS

WO        2009/013596 A2    1/2009

OTHER PUBLICATIONS

Dell'Agli et al., "Olive Oil Phenols Modulate the Expression of Metalloproteinase 9 in THP-1 Cells by Acting on Nuclear Factor-κB Signaling", Journal of Agricultural and Food Chemistry, vol. 58, No. 4, pp. 2246-2252 (2010).*
Czerwinska, M., et al., "Oleacein From Virgin Olive Oil May Contributes to Stabilization of Atherosclerotic Plaques by Decrease Myeloperoxidase Release From Neutrophils," EAS2012 Abstract Book, p. 1108, May 29, 2012.
Kiss, A.K., et al., "Dual inhibition of metallopeptidases ACE and NEP by extracts, and iridoids from *Ligustrum vulgare* L.," Journal of Ethnopharmacology, vol. 120, 2008, pp. 220-225.
Czerwinska, M., et al., "A comparison of antioxidant activities of oleuropein and its dialdehydic derivative from olive oil, oleacein," Food Chemistry, vol. 131, No. 3, Sep. 20, 2011, pp. 940-947.
International Search Report from International Patent Application No. PCT/EP2013/064869 dated Sep. 2, 2013 (3 pages).

* cited by examiner

*Primary Examiner* — Kevin E Weddington
(74) *Attorney, Agent, or Firm* — Kilyk & Bowersox, P.L.L.C.

(57) ABSTRACT

A description and explanation is provided of the use of oleacein, especially this obtained from *Ligustrum vulgare L.*, in the manufacturing of a preparation for the treatment and prevention of diseases that are consequences of the atherosclerotic plaque degradation. Such diseases include in particular those selected from the following group: ischemic brain stroke, heart attack and ischemic heart disease.

4 Claims, 2 Drawing Sheets

Figure 1:
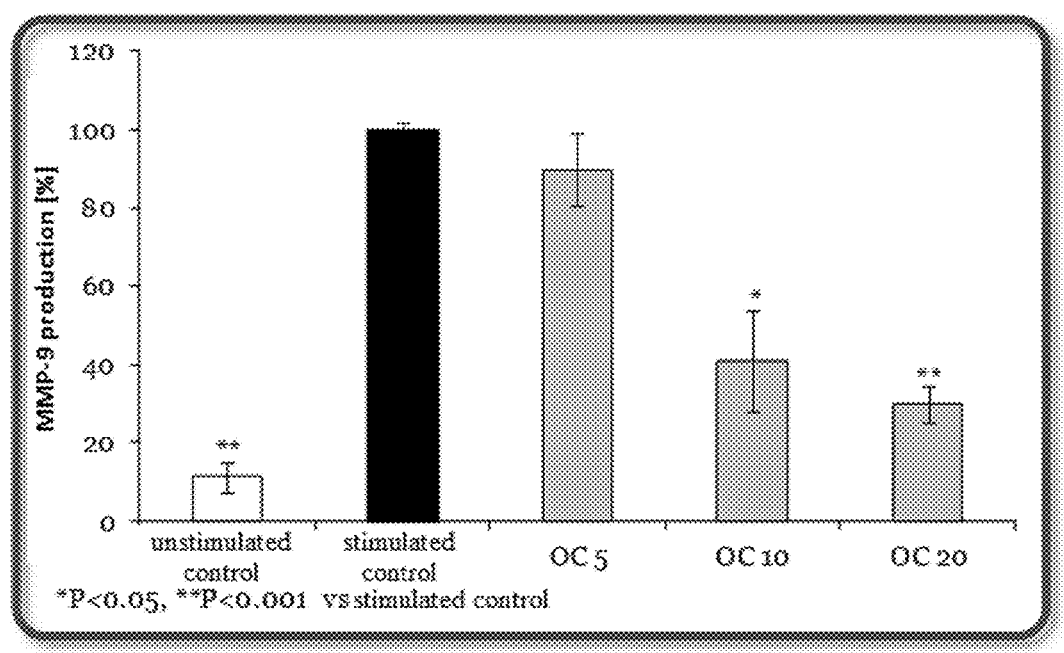

OLEACEIN FOR TREATING OR PREVENTING DISEASES RESULTING FROM ATHEROSCLEROTIC PLAQUES

This application is a National Stage Application of PCT/EP2013/064869, filed Jul. 13, 2013.

The subject of this invention is a novel use of oleacein in the manufacturing of a preparation stabilizing atherosclerotic plaque. Such a preparation may be used in particular in the prevention and treatment of diseases caused by the degradation of atherosclerotic plaque, most specifically cerebral ischemic stroke and cardiac arrest. Oleacein is a compound defined by formula 1, also described in literature as 3,4-DHPEA-EDA. It constitutes a 3,4-dihydroksyfenyloetanol (hydroxytyrosol) esterified with a dialdehyde derivative of enolic acid.

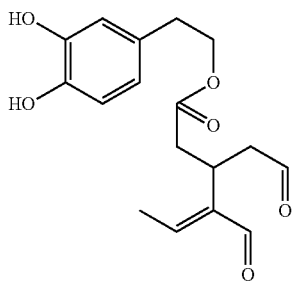

Formula 1

Atherosclerotic plaque is the name attributed to changes occurring in arterial walls (interior epithelium), which form in atherosclerosis. The plaque is composed of lipid mass (mainly LDL), cells and fibrin. It is convexed into the blood vessel lumen, decreasing its diameter. This, in turn, may lead to the ischemia of tissues supplied by the said artery.

Uncontrolled degradation of amassed atherosclerotic plaque, along with the progression of atherosclerosis in arteries, mainly in the aorta, coronary and cranial arteries, and less often in limb arteries, may become the direct cause of serious consequences such as ischemic cerebral stroke or heart ischemia. Atherosclerotic plaque may crack, activating serum thrombotic factors, which leads to clot formation. This may decrease vessel capacity, and in extreme cases completely occlude the vessel lumen. This is the most common manner in which the coronary artery is closed off, and in consequence heart attacks occur. In a similar fashion, the occlusion of a cerebral artery, as a result of the degradation of atherosclerotic plaque, leads to cerebral ischemic strokes. Limb ischemia may occur via a similar path.

Atherosclerotic plaque also damages deeper layers of artery walls, contributing to the formation of aneurysms.

For this reason, it is desirable, in patients suffering from atherosclerosis, to stabilize atherosclerotic plaque. It is also desirable to stabilize damaged atherosclerotic plaque in order to decrease its rate of degradation, and thus to lessen the course of a heart attack or brain stroke.

It is generally accepted that a key role in the degradation of atherosclerotic plaque is played by extracellular metalloproteinases released by macrophages. Among these, metalloproteinase-9 (MMP 9) is responsible for the degradation of gelatine as well as type IV and V collagen, which leads to a weakening of the fibrous sheath of atherosclerotic plaque and to its degradation (Fatar M, Stroick M, Griebe M, Hennerici M. Matrix metalloproteinases in cerebrovascular diseases. Cerebrovasc Dis 2005; 20:141-51).

The goal of this invention is to deliver a preparation which could be used to stabilize atherosclerotic plaque through the successful inhibition of its degradation in the presence of metalloproteinase-9. Such a preparation could be used in the treatment and prevention of diseases arising from the degradation of atherosclerotic plaque, in particular heart attacks, coronary ischemic disease, ischemic brain stroke and limb ischemia.

Most unexpectedly, it turned out that thus formulated stated goal has been realised by the subject of this invention.

The subject of this invention concerns the use of oleacein in the manufacturing of a preparation for the treatment and prevention of diseases that are consequences of the degradation of atherosclerotic plaque, in particular those selected from a group encompassing ischemic brain stroke, heart attack as well as ischemic heart disease.

The subject of this invention concerns also the use of oleacein in the inhibition of production of MMP-9 by the cells contained in atherosclerotic plaque.

Next subject of this invention concerns use of olacein for reduction of atherosclerotic plaque inflammation through a change in the phenotype of existing macrophages from pro-inflammatory M1 to anti-inflammatory M2, which is important for plaque stabilisation.

Preferably, the preparation produced is used for stabilizing atherosclerotic plaque.

Preferably, the oleacein is obtained from *Ligustrum vulgare L.*

The subject of the present invention concerns also the use of *Ligustrum vulgare L.* in the manufacturing of a preparation containing oleacein for stabilizing atherosclerotic plaque or for reduction of atherosclerotic plaque inflammation, particularly for the treatment and prevention of diseases that are consequences of the degradation of atherosclerotic plaque, in particular those selected from a group encompassing ischemic brain stroke, heart attack as well as ischemic heart disease.

Moreover, the present invention encompasses oleacein for any use selected of above-mentioned medical uses, any product for such use comprising oleacein, and any method, especially method for treatment human subject, comprising such use.

EXAMPLE 1

Obtaining Oleacein from the Leaves of Wild Privet (*Ligustrum vulgare L.*)

Wild privet (*Ligustrum vulgare L.*) is a decorative plant growing in Europe, often used for hedgerows. The isolation of oleacein contained in the leaves of wild privet was performed using a modification of the method by Kiss et al. (Journal of Ethnopharmacology 120 (2008) 220-225) in the Faculty of Pharmacognosis and Molecular Foundations of Phytotherapy of the Warsaw Medical Academy).

For the isolation, we used 400 g of degraded raw material. In the first stage, privet leaves were extracted four times with distilled water at a temperature of 30° C. in an ultrasound bath, for 30 minutes each time. The extraction was performed at a ratio of 1:10 raw material to solvent. Aqueous extracts were filtered through wool and pooled. The resulting aqueous extract was concentrated through lyophilisation to a volume of about 1l. In order to obtain a less contaminated extract and to increase the efficiency of the extraction process of the desirable compound, we used diethyl ether instead of ethyl acetate. Earlier analyses had shown that an ethyl acetate extraction contains more chemical compounds, thereby making the isolation of oleacein more difficult. Consequently, we then subjected the condensed aqueous extract to a 5-fold diethyl ether extract at a ratio of 1:1 solvent to extract. The ether extract was concentrated on a rotary evaporator under reduced pressure, at a temperature of 35° C. We obtained about 5 g of ether extract. The next modification was based on the use of an apparatus and reagents in an isocratic system. According to Kiss et al. (2008), purification of the ethyl acetate extract consisted of the use of a column filled with silica gel (0.125-0.25 mm; 5.5 cm×10 cm) using a solvent gradient of chloroform-ethyl acetate (100-0%) as well as ethyl acetate-methanol (100-0%). In the modified method, the ether extract was separated using flash chromatography in a column filled with silica gel (PF-30 SIHP/80G PuriFlash) using a mixture of chloroform and ethyl acetate (85:15) in an isocratic system for 60 minutes (20 ml/min). We obtained 9 fractions, from which fractions 3 and 4 were selected for subsequent separation. These fractions were further separated on a column filled with silica gel (PF-30 SIHP/80G PuriFlash) using a mixture of toluene, methyl acetate and methanol (84:11:5) in an isocratic system for 60 minutes (20 ml/min). We obtained 5 fractions, and from fraction 3, loaded onto a column filled with sephadex, we isolated oleacein using a mixture of chloroform and methanol (9:1), like in the original method. Thus we obtained 1.289 g of the compound. Identity of the compound was confirmed using NMR (See FIG. 1) as well as HPLC-DAD-MS/MS (See FIG. 2).

comparison to the stimulated control. $IC_{50}$, i.e. concentration of the compound at which reaction is inhibited by 50%, was determined at a level of 9.07±1.2 µM (average±standard error).

Figure 2:
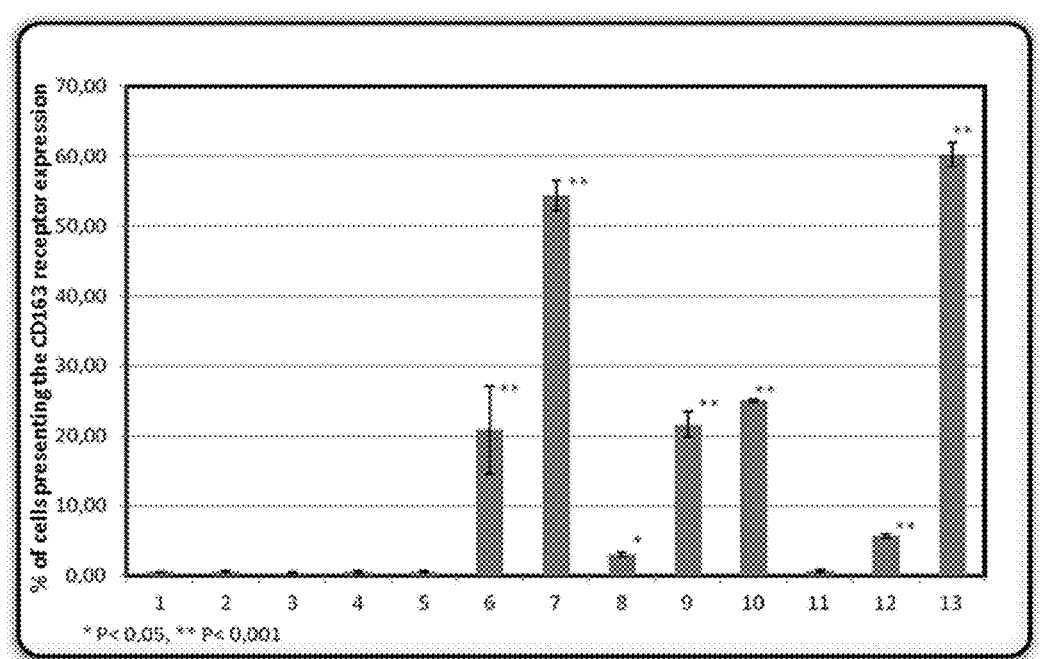

The graph included in FIG. 1 shows the dependence of MMP-9 production [%] on respective oleacein concentrations (5, 10, 20 µM).

The experimental results demonstrate the ability of oleacein to inhibit the production of MMP-9 by the cells contained in atherosclerotic plaque. The lowering of MMP-9 production stabilizes atherosclerotic plaque and retards its degradation. In connection with the effect obtained, oleacein may be used in the treatment and prophylaxis of diseases that are consequences of the degradation of atherosclerotic plaque, in particular ischemic brain stroke, heart attack as well as ischemic heart disease.

EXAMPLE 3

Reduction of Atherosclerotic Plaque Inflammation

The effects of olacein on interleukin 10 (IL-10) production were investigated with the use of the ELISA immunochemical method (R&D system). The IL-10 amounts were converted into the atherosclerotic plaque mass and, subsequently, determined in % compared to the stimulated control. The investigations confirmed increased, olacein-induced IL-10 production up to about 267.1±61.5%.

| Isolation stage | Original Method | Modified Method |
| --- | --- | --- |
| 1st extraction | 4x water; ultrasonic bath; 30 min | 4x water; ultrasonic bath; 30 min |
| 2nd extraction | 5x ethyl acetate (1:1) | 5x diethyl ether (1:1) |
| 1st separation | Water; glass column (0.125-0.25 mm; 5.5 cm × 10 cm); gradient chloroform-ethyl acetate (100-0%) and ethyl acetate-methanol (100-0%) | Water (PF-30 SIHP/80G PuriFlash); flash-type chromatography; isocratic system of chloroform and ethyl acetate (85:15) |
| 2nd separation | | Water (PF-30 SIHP/80G PuriFlash); flash-type chromatography; isocratic system of chloroform and ethyl acetate (85:15) |
| Final purification | Sephadex; glass column (2 × 25 cm); isocratic system of chloroform-methanol (9:1) | Sephadex; glass column (2 × 45 cm); isocratic system of chloroform-methanol (9:1) |

EXAMPLE 2

Stabilization of Atherosclerotic Plaque Isolated from Carotid Artery

Atherosclerotic plaques (n=15) were obtained from patients subjected to endoartherectomy. The plaque obtained was divided into two portions, which were then incubated in buffered physiological saline (control), or buffered physiological saline in the presence of oleacein at the concentrations of 5, 10 and 20 µM for 24 hours at a temperature of 37° C. following prior stimulation with a solution of lipopolysaccharide at a concentration of 1 µg/ml. The unstimulated control consisted of physiological saline, in which the plaque was incubated for 2 hours. The effect of oleacein on metalloproteinase-9 (MMP-9) production was determined using immunochemical ELISA (R&D System). The amount of MMP-9 (ng/ml) was calculated per mass of atherosclerotic plaque, and then described in terms of percentage in In diseases like diabetes, atherosclerosis and other pathological conditions in a human body, there is no change in the CD163 receptor expression in macrophage cells due to haemoglobin-haptoglobin complexes, which prevents from a change in the phenotype of these cells. The pro-inflammatory macrophages have a destabilising effect on the atherosclerotic plaque and cause microbleeding.

Oleacein-haemoglobin (OC+Hb) complexes induce the expression of the macrophage scavenger receptor CD163, which leads to a change in the macrophage phenotypes from the pro-inflammatory M1 form to the anti-inflammatory M2 type. This process significantly affects the atherosclerotic plaque stabilisation in human arteries.

The changes in the macrophage receptor CD163 expression, resulting from macrophage cell stimulation by various agents, were assayed with the use of flow BD FACSCalibur flow cytometer. The findings are presented in the FIG. 2. Symbol description: 1—K-control, 2—Hb-haemoglobin, 3—Hp-haptoglobin, 4—OC 10-oleacein in 10 µM, 5—OC 20-oleacein in 20 μM, 6—OC 10+Hb–haemoglobin-olacein complex in 10 μM, 7—OC 20+Hb–haemoglobin-olacein complex in 20 μM, 8—Hb+Hp 1-1–haemoglobin-1-1 haptoglobin complex, 9—OC 10+Hb+Hp 1-1–olacein-haemoglobin-1-1 haptoglobin complex in 10 μM, 10—OC 20+Hb+Hp 1-1–olacein-haemoglobin-1-1 haptoglobin complex in 20 μM, 11—Hb+Hp 2-2–haemoglobin-2-2 haptoglobin complex, 12—OC 10+Hb+Hp 2-2–olacein-haemoglobin-2-2 haptoglobin complex in 10 μM, 13—OC 20+Hb+Hp 2-2–olacein-haemoglobin-2-2 haptoglobin in 20 μM.

The invention claimed is:

1. A method for inhibiting MMP-9 production by atherosclerotic plaque cells in a patient, said method comprising administering oleacein to said patient, wherein said oleacein is obtained from *Ligustrum vulgare* L.

2. The method of claim 1, wherein said inhibiting stabilizes atherosclerotic plaque and causes a change in phenotype of existing macrophages from pro-inflammatory M1 to anti-inflammatory M2.

3. The method of claim 1, wherein said oleacein is an extract.

4. The method of claim 1, wherein said oleacein is an aqueous extracted oleacein.

* * * * *